United States Patent
Mauvernay

(10) Patent No.: US 6,866,857 B1
(45) Date of Patent: Mar. 15, 2005

(54) OXALIPATINUM PREPARATION PACKAGING

(75) Inventor: Rolland-Yves Mauvernay, Lausańne (CH)

(73) Assignee: Debiopharm S.A. (CH)

( * ) Notice: Subject to any disclaimer, the term of this patent is extended or adjusted under 35 U.S.C. 154(b) by 0 days.

(21) Appl. No.: 09/807,586

(22) PCT Filed: Oct. 13, 1999

(86) PCT No.: PCT/IB99/01670

§ 371 (c)(1),
(2), (4) Date: Jul. 11, 2001

(87) PCT Pub. No.: WO00/21527

PCT Pub. Date: Apr. 20, 2000

(30) Foreign Application Priority Data

Oct. 14, 1998  (CH) ............................................. 2067/98

(51) Int. Cl.⁷ ........................ A01N 25/34; A61M 5/178; A61B 19/00
(52) U.S. Cl. ...................... 424/402; 514/492; 604/212; 604/410; 604/416
(58) Field of Search ........................ 424/402; 604/212, 604/410, 416; 514/492; 206/231, 484.2, 219, 221

(56) References Cited

U.S. PATENT DOCUMENTS

| 4,169,846 A |   | 10/1979 | Kidani et al. |   |
|---|---|---|---|---|
| 5,492,534 A | * | 2/1996 | Athayde et al. | 604/141 |
| 5,716,988 A | * | 2/1998 | Ibrahim et al. | 514/492 |
| 6,007,529 A | * | 12/1999 | Gustafsson et al. | 604/410 |
| 6,306,902 B1 | * | 10/2001 | Anderson et al. | 514/492 |

FOREIGN PATENT DOCUMENTS

| WO | WO 98/39009 | 2/1998 |
|---|---|---|
| WO | WO 99/43355 | 2/1999 |

OTHER PUBLICATIONS

Who Drug Information, vol. 1, No. 4, 1987, pp. 195, 240–241, 248–249.

* cited by examiner

*Primary Examiner*—Thurman K. Page
*Assistant Examiner*—Isis Ghali
(74) *Attorney, Agent, or Firm*—Piper Rudnick LLP

(57) ABSTRACT

Flexible impervious bag for medical use containing a pharmaceutical preparation of liquid oxaliplatinum said flexible bag is constructed from plastic materials, with the proviso that any portion to the bag in direct contact with said pharmaceutical preparation of liquid oxaliplatinum does not contain polyvinylchloride-based plastic material.

5 Claims, 6 Drawing Sheets

120  20  60  Microns
PP   PP  PA

OXALIPATINUM PREPARATION PACKAGING

The invention concerns a pharmaceutical preparation of oxaliplatinum packaged in a container, preferably in a sealed soft (flexible) bag for medical use.

The optically active complex of platinum, cis-oxalato (trans-1-1-diaminocyclohexane) platinum(II), under its international nonproprietary name (INN) "oxaliplatinum", is known to possess anti-tumor properties and its preparation was described in the patent U.S. Pat. No. 4,169,846.

Oxaliplatinum, like other platinum complexes such as Cisplatin or Carboplatin, is used as an antineoplastic, cytostatic agent for the therapeutic treatment of various types of cancer. These include, *inter alia*, cancer of the colon, ovaries, tipper respiratory passages or epidermal (skin) cancers as well as germ cell tumors (testes, mediastinum [interpleural space], pineal gland etc.). The use of oxaliplatinum is particularly appropriate for the treatment of colon cancers that are resistant to pyrimidines, of small cell lung cancers, non-Hodgkin lymphomas, breast cancers, cancers of the upper respiratory-digestive passages, malignant melanomas, liver carcinomas, uro-epithelial cancers, cancers of the prostate etc.

International Patent Application WO 96/04904 describes a pharmaceutical preparation of oxaliplatinum in aqueous solution. This preparation has the advantage of obtaining a ready-to-use, injectable solution of oxaliplatinum that is simpler and more reliable in use and less expensive to manufacture than a preparation starting with a lyophilisate (freeze-dried substance). It has a chemical purity (no racemisation) and therapeutic activity equivalent to or greater than those obtained by starting with a reconstituted lyophilisate.

This pharmaceutical preparation was stored in bottles made of neutral glass for pharmaceutical use under an inert gas atmosphere. However, such bottle packages, although appropriate for long-term storage of the pharmaceutical preparation, are unsuitable for containing this preparation during administration by perfusion.

Flexible bags consisting of a material based on polyvinylchloride (PVC) are used during perfusion procedures of liquid preparations of platinum complexes other than oxaliplatinum, such as cisplatin or carboplatin.

However, and in contrast to what has been observed for liquid preparations of cisplatin and carboplatin, it has been found that particularly because of their greater chemical sensitivity, pharmaceutical preparations of oxaliplatinum in aqueous solution cannot tolerate being in contact with PVC-based materials, nor can, they be transported and/or stored in containers, especially flexible bags based on these materials.

The aim of the present invention is to provide liquid pharmaceutical preparations of oxaliplatinum that can not only be stored for a long period of time without any detectable loss of quality but can also be used in particular for perfusion procedures without any need for the nursing personnel to perform an operation to decant liquid pharmaceutical preparations.

For this purpose, the present invention concerns a liquid pharmaceutical preparation of oxaliplatinum as set forth in the appended claims.

The invention will be set out below with the help of the Drawings in which

The pharmaceutical preparation of oxaliplatinum according to the present invention is stored, then used directly, in a flexible bag constructed from plastics materials chosen from among polyethylenes (PE), polypropylenes (PP), polyethyl and polyvinyl acetates polyamides (PA) and polyisobutyls (PIB). Latex (rubber) can also be used.

Figure 1:
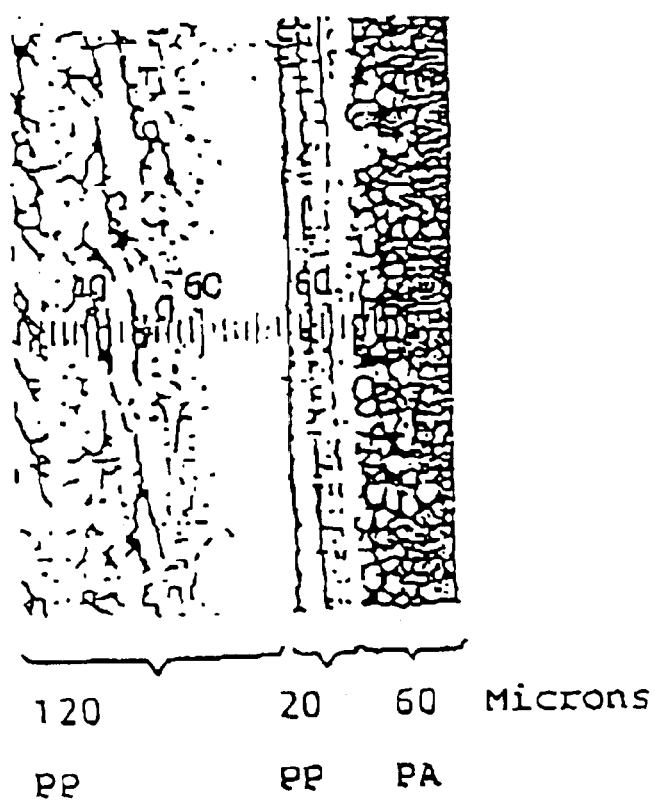
FIG. 1 shows a cross-sectional view of the envelope of the flexible bag used in the invention.

As shown in FIG. 1, the envelope of the bag preferably has a multi-layer structure. More preferably, the internal layer in direct contact with the pharmaceutical preparation consists of PP and the external layer or possible intermediate layers can consist of any of the above-mentioned plastic. The external layer or the possible intermediate layers can even consist of PVC, the oxaliplatinum not being in direct contact with this material.

Figure 2:
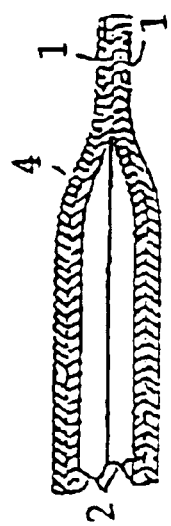
FIG. 2 shows a cross-sectional view of the flexible hag used in the invention.

As shown in FIG. 2 and according to a particular embodiment of the invention, the flexible bag can consist of welded sheets of multi-layer materials. Preferably the flexible bay can consist of at least two sheets welded together. More preferably, this bag can consist of two welded sheets of multi-layer sheet materials comprising, one film of 11-amino-undecanoic acid (PA 11) bonded by at least one of its surfaces to a film of PP by the use of a polyolefin film the PP films forming the internal wall of the leakproof flexible bag.

The flexible bag of the invention preferably consists of a material comprising 70% of PP and 30% of PA 11 and commonly called V90.

Astonishingly it has been found, during a physico-chemical study performed before and after the sterilisation procedure and comparing the liquid phase water permeability properties of flexible bag envelopes consisting firstly of PVC and secondly of V90, that the bags based on V90 material constitute an excellent barrier to water loss generally due to evaporation. This property is not found in the classical PVC bags, not even those using PVC as a constituent of the inner layer.

Figure 3:
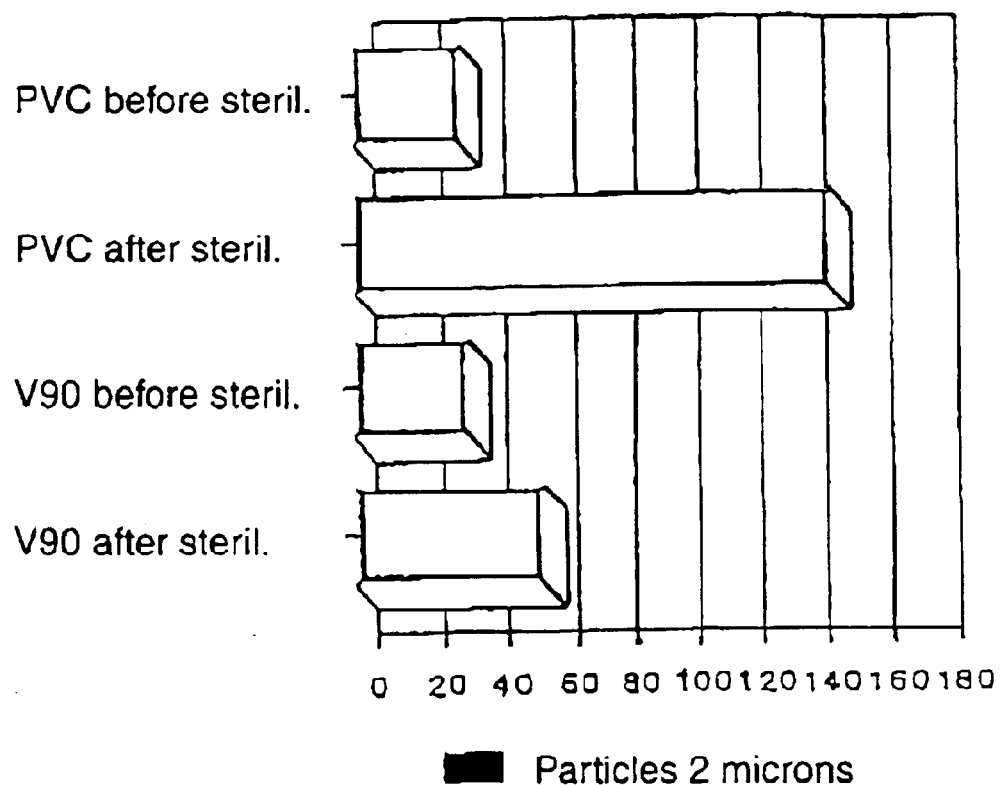
FIG. 3 shows a comparison graph of the liquid phase water permeability firstly of PVC and secondly of a suitable construction material for the envelope of the flexible bag used in the invention, before and after a sterilisation procedure.

The results of this study are shown diagrammatically by the graph of FIG. 3.

Figure 4:
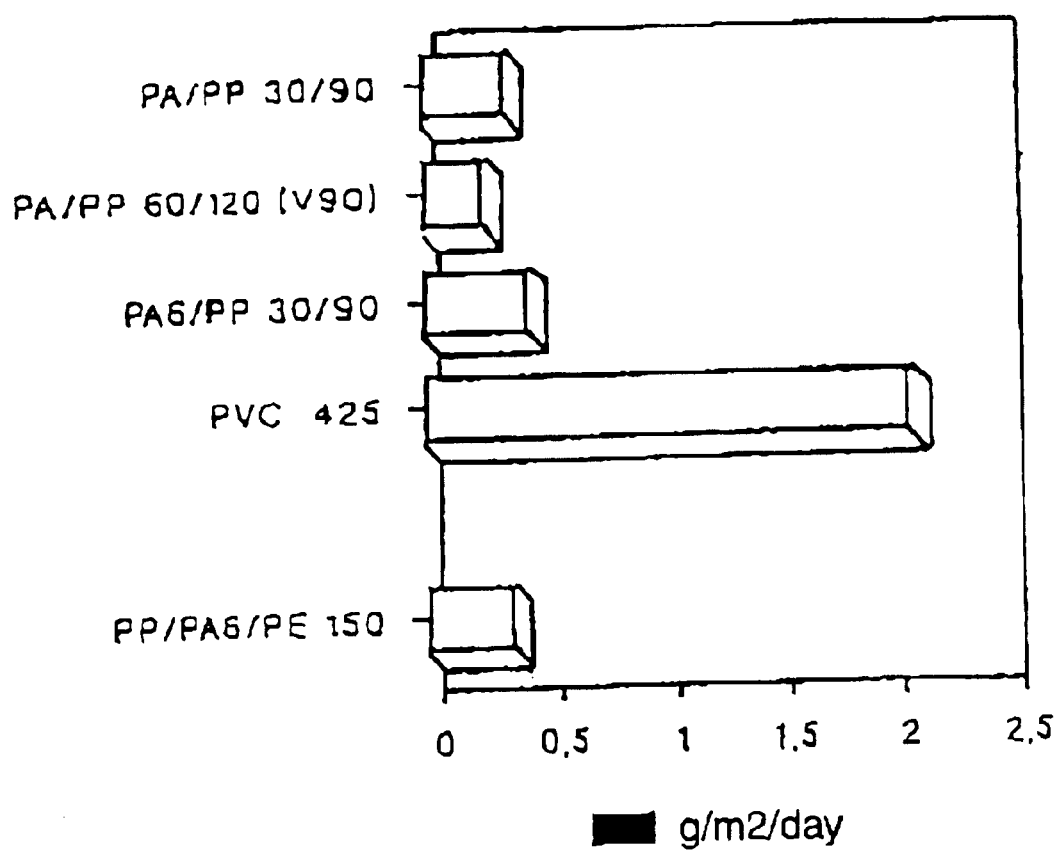
FIG. 4 shows a comparison graph of the vapour phase water permeability of various suitable construction materials for the envelope of the flexible bag used in the invention, before and after a sterilisation procedure.

During a second study comparing the vapour phase water permeability properties of PVC and various construction materials for the flexible bags used in the invention, the material V90 proved to be the most leak-tight (impervious) as shown by the diagram in FIG. 4.

Such properties of imperviousness to water in its two forms, liquid and vapour, are extremely important when contemplating the use of such a material for the construction of the flexible bags used for the invention. In fact, the almost zero losses of water guarantee the maintenance of an almost constant concentration of the pharmaceutical preparations of oxaliplatinum over time. Excessive packaging of the envelope of the bag used for the invention is thus unnecessary.

Figure 5:
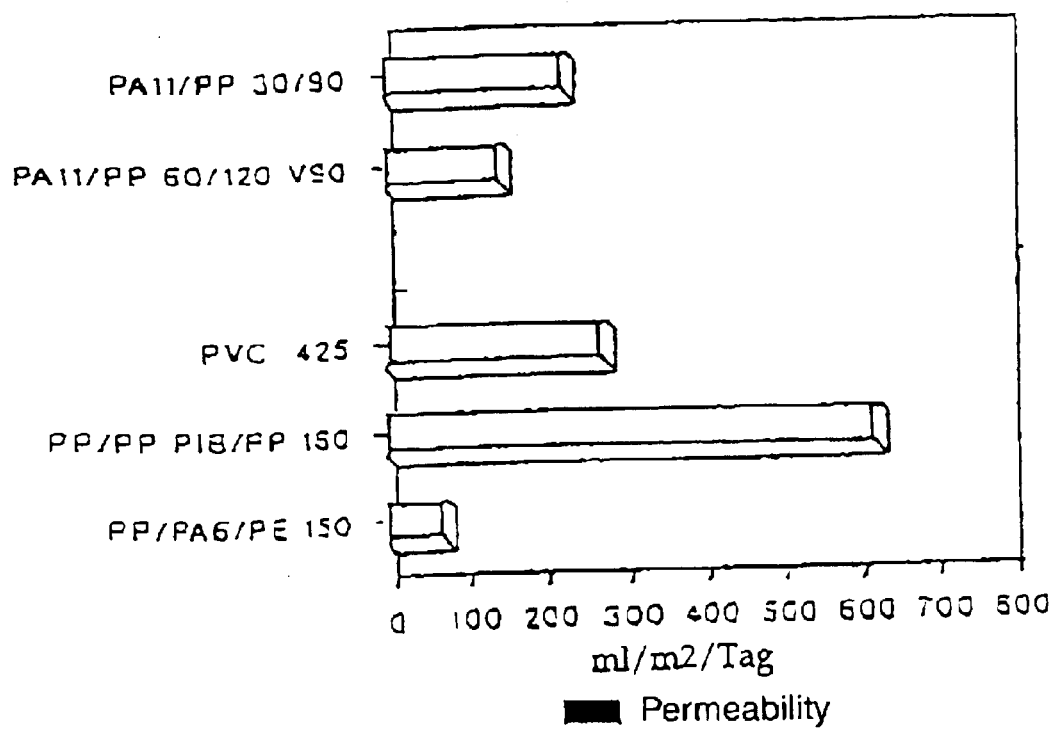
FIG. 5 shows a comparison graph of the oxygen permeability of various suitable construction materials for the envelope of the flexible bag used in the invention, before and after a sterilisation procedure.

The impermeability to oxygen of the V90 material was also studied and compared to that of PVC, and proved to be at a far superior level. The results of studied comparative study are shown diagrammatically in FIG. 5.

This property of impermeability to oxygen is very important in view of the sensitivity of oxaliplatinum to oxidising substances, the degradation products generated during such oxidation generally being inactive from the pharmacological point of view and may even be toxic to the organism. This property is very suitable during the use of the flexible bag, which has the advantage compared to glass bottles of not needing the presence of an inert gas atmosphere.

A test of the stability of the liquid solution of oxaliplatinum (Tanaka K. K., Batch I.o 92 TO 34) was carried out. To do this, 100 ml bags consisting of PA 11/PP 60/140 and measuring 13.0×12.5 cm were used. The hags contained 200 m, of oxaliplatinum at a concentration of 2 mg/ml, i.e. 100 ml of liquid Oxaliplatinum solution per bag. This test was performed over a total or 12 weeks in accordance with the sampling plan. The bags were subjected to what are called accelerated storage conditions at a temperature of 40° C. and a relative humidity (R11) of 75%.

The results of this accelerated stability study are summarised in Table 1

| Kinetic parameters | Week 0 | Week 1 | Week 2 | Week 3 | Week 4 | Week 5 | Week 12 | 6 Months | 12 Months |
| --- | --- | --- | --- | --- | --- | --- | --- | --- | --- |
| Appearance of the solution | Clear, colourless | Clear, colourless | Clear, colourless | Clear, colourless | Clear, colourless | Clear, colourless | Clear, colourless | Clear, colourless | Clear, colourless |
| L-OHP titre/standard (%) | 99.7 | 100.1 | 100.0 | 100.9 | 99.3 | 97.7 | 99.3 | 98.9 | 98.5 |
| Oxalic acid titre (%) | <0.1% | <0.1% | <0.1% | <0.1% | <0.1% | <0.1% | <0.1% | <0.1% | <0.1% |
| Visible impurities (%) | 0.10 | 0.60 | 0.50 | 0.50 | 0.48 | 0.45 | 0.40 | 0.5 | 0.6 |
| pH | 5.56 | 5.10 | 5.24 | 5.22 | NM | 5.23 | 5.35 | 5.20 | 5.30 |

NM = Not measured

The V90 material also affords the advantage from the ecological point of view of being recyclable and reusable in another form, which is not the case with PVC.

Another attractive aspect of the use of the aforementioned materials, particularly PP (V90), lies in the ability to make leak-tight welds very easily. In this way it is possible to obtain flat compartmented bags. This property is not achievable with a PVC material, which requires the use of connectors to communicate between the various compartments. Unfortunately these connectors are a source of leaks, which is not observed in the case of bugs made of PP (V90).

These compartments can be multiple so as to allow the mixing of different solutions. These compartments can contain the solution already ready for use, at the right dose, and can be withdrawn or used directly by the medical personnel without the risk of error.

The aforesaid materials, particularly PP (V90), also have the advantage of withstanding high temperatures better. This is particularly attractive during the sterilisation of flexible bags containing a solution of oxaliplatinum by autoclave. This sterilisation is much simpler because the exposure tire can be reduced by increasing the temperature.

The liquid oxaliplatinum solution contained in the bags preferably has a concentration between 1 and 8 mg/ml. According to one particular embodiment of the invention the oxaliplatinum concentration lies between 1 and 5 mg/ml at a pH between 4 find 7, ideally between 4.5 and 6.0.

According to one particular embodiment of the invention the concentration of oxaliplatinum in the preparation contains at least 95% of the initial concentration and has a clear, colourless appearance free from precipitate after storage during a pharmaceutically acceptable period.

In a surprising manner the liquid solution of oxaliplatinum packed in a flexible bag is stable for a period extending to more than three months, and even to more than six months.

Astonishingly, this liquid solution of oxaliplatinum packed in a flexible ban appears to remain stable for at least one year.

The appearance of the solution was observed for twelve months, and to our great astonishment showed clarity and the absence of coloration over the whole of this period. Analysis of the concentrations was performed by high pressure liquid chromatography (HPLC=High Performance Liquid Chromatography).

As far as the concentration of oxaliplatinum is concerned, a stated quantity lying between 95 and 105% was obtained, taking into account the limit of resolution of the system. As far as the determination of oxalic acid is concerned, the maximum limit is 0.5% by the HPLC method.

The maximum percentage of apparent impurities determined in the same way was 2%.

Figure 6:
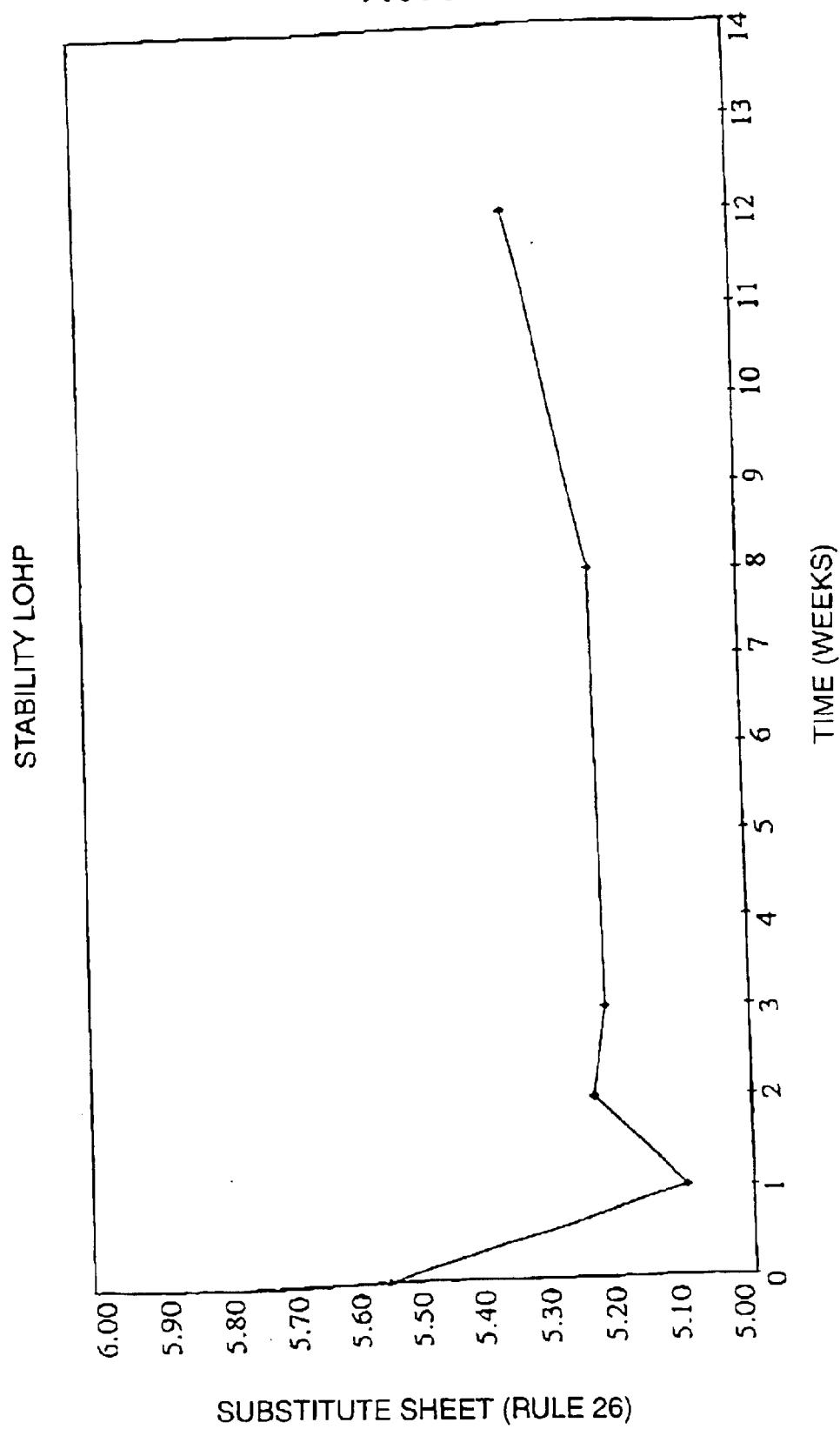
FIG. 6 shows the pH variation over time of a preparation according to the invention.
Figure 7:
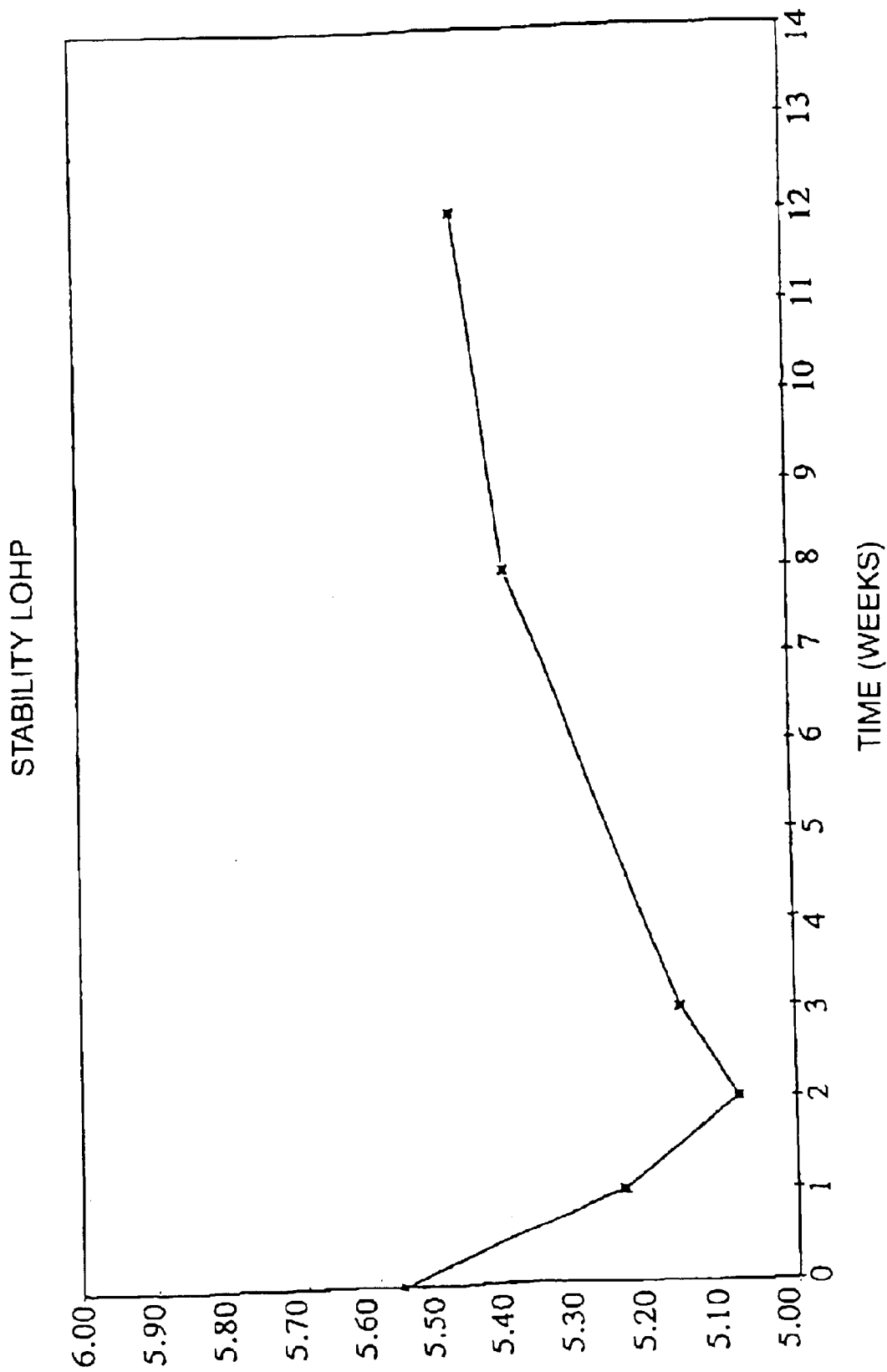
FIG. 7 shows the pH variation over time of a liquid pharmaceutical solution of oxaliplatinum stored in a glass bottle under an inert gas atmosphere.

FIG. 6 shows the development of the pH over 12 weeks. This pH lies between 4.7 and 5.9, and varies very little with time, which is good proof that the oxaliplatinum solution remakes stable in this type of bag. This system shows a stability analogous to that observed for a solution of oxaliplatinum subjected to the same conditions and packed in a glass bottle, as FIG. 7 shows.

All of the above results show consistently that pharmaceutical preparations of oxaliplatinum can be stored in flexible bags for a long period without any chemical degradation of the oxaliplatinum being observed, from the moment they are no longer in direct contact with PVC-based material. Because of the flexibility of the materials of which the bags consist, such preparations are ready to the used for transfusion procedures without any decanting operation being necessary.

What is claimed is:

1. Flexible impervious bag for medical use containing a pharmaceutical preparation of liquid oxaliplatinum, said bag having a multi-layer structure comprising an outer envelope and/or internal layers, with the proviso that any portion of the bag in direct contact with said pharmaceutical preparation of liquid oxaliplatinum does not contain polyvinylchloride-based plastic material, wherein said flexible bag consists of two welded sheets of multi-layer sheet material comprising as its outer envelope a film of polyamide of 11-amino-undecanoic acid bonded by at least one of its surfaces to a film of polypropylene by means of a film of polyolefin, the polypropylene film forming the internal layer of the flexible bag.

2. Flexible impervious bag for medical use containing a pharmaceutical preparation of oxaliplatinum according to claim 1, wherein the concentration of oxaliplatinum in the pharmaceutical preparation is between 1 and 8 mg/ml.

3. Flexible impervious bag for medical use containing a pharmaceutical preparation of oxaliplatinum according to claim 1, wherein the concentration of oxaliplatinum in the pharmaceutical preparation is between 1 and 5 mg/ml.

4. Flexible impervious bag for medical use containing a pharmaceutical preparation of oxaliplatinum according to claim 1, wherein said solution has a pH of 4.5 to 6.0, a concentration of oxaliplatinum in the preparation of at least 95% of the initial concentration, as well as a clear, colourless appearance free from precipitate after storage for a pharmaceutically acceptable period.

5. Flexible impervious bag for medical use containing a pharmaceutical preparation of oxaliplatinum, wherein said bag consists of a material comprising 70% polypropylene and 30% 11-amino-undecanoic acid.

* * * * *